US005641629A

United States Patent [19]

Pitner et al.

[11] Patent Number: 5,641,629

[45] Date of Patent: Jun. 24, 1997

[54] SPECTROSCOPICALLY DETECTABLE NUCLEIC ACID LIGANDS

[76] Inventors: James B. Pitner, Rte. 5 Box 92, Durham, N.C. 27704; Douglas P. Malinowski, 1005 Dimmocks Mill Rd., Hillborough, N.C. 27278; Glenn P. Vonk, 2717 Piney Grove-Wilbon Rd., Fuquay-Varina, N.C. 27527; Larry Gold, 1033 5th St., Boulder, Colo. 80302

[21] Appl. No.: 376,329

[22] Filed: Jan. 20, 1995

Related U.S. Application Data

[63] Continuation-in-part of Ser. No. 276,271, Jul. 18, 1994, which is a continuation-in-part of Ser. No. 234,997, Apr. 28, 1994, and a continuation-in-part of Ser. No. 443,957, May 18, 1995, Pat. No. 5,580,737, which is a continuation of Ser. No. 134,028, Oct. 7, 1993, abandoned, which is a continuation-in-part of Ser. No. 931,473, Aug. 17, 1992, Pat. No. 5,270,163, which is a division of Ser. No. 714,131, Jun. 10, 1991, Pat. No. 5,475,096, which is a continuation-in-part of Ser. No. 536,428, Jun. 11, 1990, abandoned.

[51] Int. Cl.[6] .............................. C12Q 1/68; C07H 21/02; C07H 21/04

[52] U.S. Cl. .................................. 435/6; 935/77; 935/78; 536/22.1

[58] Field of Search ................................ 435/6, 91.2, 7.1, 435/7.8, 7.93; 935/77, 78

[56] References Cited

U.S. PATENT DOCUMENTS

| | | | |
|---|---|---|---|
| 3,998,943 | 12/1976 | Ullman et al. | 435/7.1 |
| 4,777,129 | 10/1988 | Dattagupta et al. | 435/6 |
| 5,047,321 | 9/1991 | Loken et al. | 435/6 |
| 5,270,163 | 12/1993 | Gold et al. | 435/6 |

FOREIGN PATENT DOCUMENTS

| | | |
|---|---|---|
| 2 183 661 | 6/1987 | United Kingdom . |
| WO89/06694 | 7/1989 | WIPO . |

OTHER PUBLICATIONS

Joyce (1989) Gene 82:83.

Joyce and Inoue (1989) Nucleic Acids Research 17:711.

Ellington and Szostak (1990) Abstract of papers presented at the 1990 meeting on RNA Processin, Cold Spring Harbor Laboratory, Cold Spring Harbor, NY, p. 226.

Kinzler and Vogelstein (1989) Nucleic Acids Research 17:3645.

Kramer et al. (1974) J. Mol. Biol. 89:719.

Levisohn and Spiegelman (1969) Proc. Natl. Acad. Sci. USA 63:805.

Levisohn and Spiegelman (1968) Proc. Natl. Acad. Sci. USA 60:866.

Oliphant et al. (1989) Mol. Cell. Biol. 9:2944.

Oliphant and Struhl (1988) Nucleic Acids Research 16:7673.

Oliphant and Struhl (1987) Methods in Enzymology 155:568.

Oliphant et al. (1986) Gene 44:177.

Robertson and Joyce (1990) Nature 344:467.

Thiesen and Bach (1990) Nucleic Acids Research 18:3203.

Bock et al. (1992) Nature 355:564–566.

Soini et al. Clin. Chem. 25(3):353–361(1929).

Tizard, *Immunology:An Introduction*, 2d Ed., Sonnden College Publ., Phila., 1988 (pp. 116–117).

*Primary Examiner*—Stephanie W. Zitomer
*Attorney, Agent, or Firm*—Swanson & Bratschun, L.L.C.

[57] ABSTRACT

The present invention relates to methods of using spectroscopically detectable labeled receptor molecules to determine the presence or absence of a target compound in a sample. In one embodiment, spectroscopically detectable labeled nucleic acid ligands are used to determine the presence or absence of biological targets of interest in biological samples.

36 Claims, 6 Drawing Sheets

GGTTGGTGTG
GTTGG-3'
(SEQ ID NO:1)

COMPOUND 1

CAGTCCGTGGTAGGGC
AGGTTGGGGTGACTTCG
TGGAA-3' (SEQ ID NO:2)

COMPOUND 2

GGTTGGTGTG
GTTGG-3'
(SEQ ID NO:1)

COMPOUND 3

GGTGGTGGTTGTGGT-3'
(SEQ ID NO:3)

COMPOUND 4

TAGCGATACTGCGTG
GGTTGGGGCGGGTA
GGGCCAGCAGTCTC
GT-3' (SEQ ID NO:4)

COMPOUND 5

5'-GGTTGG
TGTGGTTGG-3'
(SEQ ID NO:1)

COMPOUND 6

SEQUENCE LISTING ( 1 ) GENERAL INFORMATION:

( i i i ) NUMBER OF SEQUENCES: 4

-continued ( 2 ) INFORMATION FOR SEQ ID NO:1:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

GGTTGGTGTG GTTGG 15

( 2 ) INFORMATION FOR SEQ ID NO:2:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:2:

CAGTCCGTGG TAGGGCAGGT TGGGGTGACT TCGTGGAA 38

( 2 ) INFORMATION FOR SEQ ID NO:3:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:3:

GGTGGTGGTT GTGGT 15

( 2 ) INFORMATION FOR SEQ ID NO:4:

( i ) SEQUENCE CHARACTERISTICS:
( A ) LENGTH: 45 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:4:

TAGCGATACT GCGTGGGTTG GGGCGGGTAG GGCCAGCAGT CTCGT 45

SPECTROSCOPICALLY DETECTABLE NUCLEIC ACID LIGANDS

RELATED DISCLOSURES

The subject application is a continuation-in-part of U.S. application Ser. No. 08/276,271, filed Jul. 18, 1994, which is a continuation-in-part of U.S. application Ser. No. 08/234,997, filed Apr. 28, 1994; and is a continuation-in-part of U.S. application Ser. No. 08/443,957, filed May 18, 1995, now U.S. Pat. No. 5,580,737, which is a continuation of U.S. application Ser. No. 08/134,028, filed Oct. 7, 1993 abandoned, which is a continuation-in-part of Ser. No. 07/931,473, filed Aug. 17, 1992, now U.S. Pat. No. 5,270,163, which is a divisional of U.S. application Ser. No. 07/714,131, filed Jun. 10, 1991, now U.S. Pat. No. 5,475,096, which is continuation-in-part of U.S. application Ser. No. 07/536,428, filed Jun. 11, 1990, now abandoned.

FIELD OF THE INVENTION

The present invention relates to the detection of the binding of target molecules to a nucleic acid ligand by spectroscopic techniques such as fluorescence polarization and fluorescence anisotropy.

BACKGROUND OF THE INVENTION

Fluorescence polarization immunoassay technology is well known in the art as evidenced by the following references:

(1) Dandliker, W. B. and Feigen, G. A., *Biochem. Biophys. Res. Commun.*, 5, 299 (1961);
(2) Jolley, M. E., *J. Anal. Toxicol.* 5, 236 (1981);
(3) Lakowicz, J. R., "Principles of Fluorescence Spectroscopy", Plenum Press, NY, (1983);
(4) "Immunoassay, a Practical Guide", Chan, D. W. and Peristein, N. T., Eds. Academic Press, NY, 1987);
(5) Price, C. and Newman, D., Chapter 14 ("Homogeneous Fluoroimmunoassay") in "Principles and Practice of Immunoassay", C. P. Price and D. J. Newman, Eds., MacMillan, NY (1991); and
(6) Wei, A -P. and Herron, J. N., *Anal. Chem.*, 65, 3372 (1993).

Fluorescence polarization immunoassays typically use fluorescently labeled target molecules. These labeled target molecules compete with the target molecules of interest for antibody binding sites. As noted by Wei and Herron, supra, fluorescence polarization immunoassays have not been applied with much success to the detection of large macromolecules such as human chorionic gonadotropin (hcg).

The basis of homogeneous fluoroimmunoassays depends upon the binding of an antibody modulating the emission of a fluorophore coupled to an antigen. A low level of fluorescence polarization resulting from the excitation of a fluorescently labeled antigen is increased as the rotation of the antigen is diminished by binding of antibody. Thus, at low sample antigen concentration, the fluorescence polarization will be greatest, reducing as sample antigen displaces fluorophore from the antibody.

Since fluorescence polarization is a measure of the time-average rotational motion of fluorescent molecules, the fluorescent labeling of antibodies to detect antigen-antibody binding has proved largely ineffective due to the disparity in size between antigen and antibody. Generally, an antibody is so much larger than an antigen that the difference in rotational motion when an antigen binds to the antibody is virtually undetectable. Therefore, conventional fluorescence polarization immunoassay technology has been confined to the fluorescent labeling of antigen or target molecule as opposed to antibody or receptor molecule.

SUMMARY OF THE INVENTION

In contrast to conventional fluorescence polarization immunoassay technology as described above, the present invention permits the use of a spectroscopically detectable labeled receptor molecule in an immunoassay-type detection system for target molecules. In one embodiment, the present invention relates to a spectroscopically detectable labeled nucleic acid ligand which is capable of binding a target molecule. When used in a detection system, this spectroscopically detectable labeled nucleic acid ligand permits the quantitative and qualitative determination of differences in detectable emissions to determine the presence or absence of a specific target molecule in a sample.

BRIEF DESCRIPTION OF THE DRAWINGS

The various objects, advantages and novel features of the invention will be more readily appreciated from the following detailed description when read in conjunction with the appended drawing figures, in which.

DETAILED DESCRIPTION OF THE INVENTION

Figure 1:
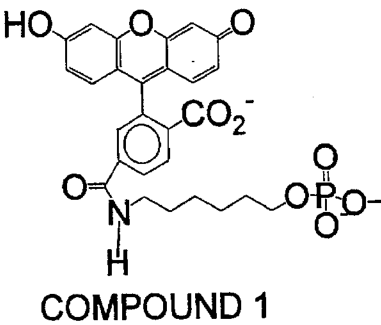
FIG. 1 shows the structural formulas of various spectroscopically detectable nucleic acid ligands.
Figure 1:
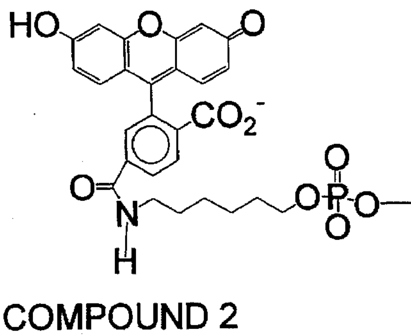
Figure 1:
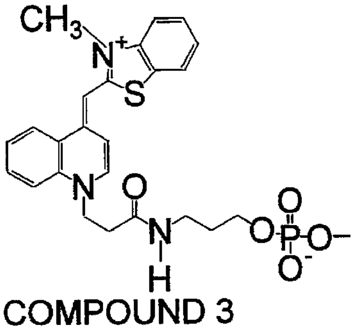
Figure 1:
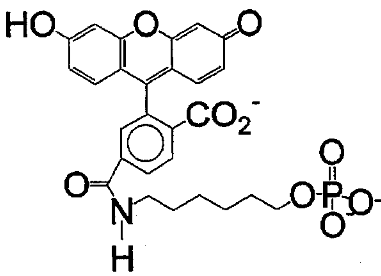
Figure 1:
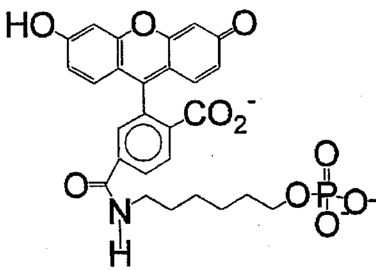
Figure 1:
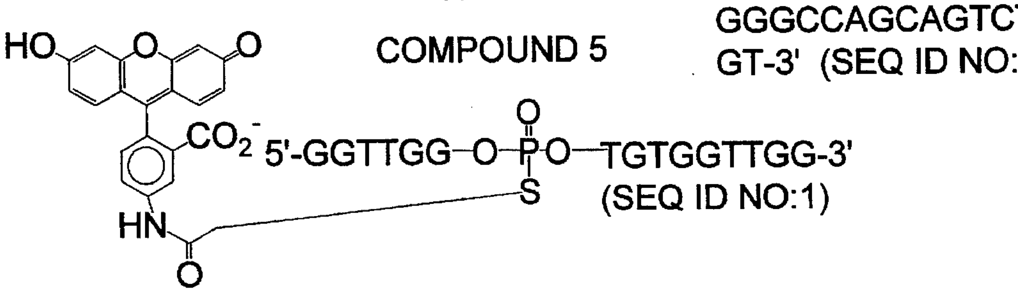

Traditionally, antibodies have been utilized as receptor molecules to bind and therefore permit the detection of target molecules (e.g. antigens) in samples. However, new classes of receptor molecules which also bind traditional target molecules in samples have recently been identified. Some of these new classes of receptor molecules include nucleic acid ligands as described in U.S. Pat. No. 5,270,163 and bi-directional nucleic acid ligand compounds as described in co-pending U.S. patent application Ser. No. 08/252,071, filed May 31, 1994.

One of the advantages of these new classes of receptor molecules for purposes of spectroscopic detection is their relatively small size in relation to traditional receptor molecules (i.e. antibodies). Due to the small size of these new receptor molecules, spectroscopically detectable labels attached thereto will exhibit significantly different energy characteristics when a target molecule is bound to the labeled receptor molecule as opposed to when there is no target bound to the receptor molecule. Due to the small size of these new receptor molecules, any additional volume or weight added thereto even in the form of a relatively small target will significantly increase the weight or volume of the labeled receptor molecule and therefore permit detection of such relatively large differences. It is this principle which is utilized in the present invention.

In one embodiment of the present invention, a detection system utilizes a spectroscopically detectable labeled nucleic acid ligand to quantitatively and/or qualitatively determine the presence of a target molecule in a sample. In another similar embodiment of the invention, a spectroscopically detectable labeled nucleic acid ligand is utilized in a competition-based assay to monitor binding of target compounds such as growth factors to their receptors. In this embodiment, the method comprises the steps of adding to the sample a spectroscopically detectable labeled nucleic acid ligand that binds to the receptor; measuring the spectroscopic emissions of the complex of receptor and spectroscopically detectable nucleic acid ligand; determining from the spectroscopic emissions of the complex the degree of binding of the spectroscopically detectable labeled nucleic acid ligand to the receptor; and calculating from the degree of binding of the spectroscopically detectable labeled nucleic acid ligand to the receptor, the degree of binding of target compound to the receptor. The principles and procedures for competition-based assays are the same as would be used in competition-based immunoassays and are well known to practitioners in the art and taught in references such as Ekins, R., "Immunoassays", *Encyclopedia of Immunology* pp. 779–782, Academic press (1992).

Numerous nucleic acid ligands which bind target molecules have been identified. These targets include proteins such as enzymes, cell-surface markers, amino acids and dyes. For example, RNA nucleic acid ligands have been identified that have high affinity and specificity for: (1) bacteriophage T4 DNA polymerase (Tuerk, C. and Gold, L., *Science* 249, 505 (1990)); (2) R17 coat protein (Schneider, D. et al., *J. Mol. Biol.* 228, 862 (1992)); (3) human immunodeficiency virus (HIV) reverse transcriptase (Tuerk, C. et al, *Proc. Nat'l. Acad. Sci. USA* 89, 6988 (1992)); (4) HIV rev protein (Bartel, D. P. et al., *Cell.* 67, 529 (1991)); (5) basic fibroblast growth factor (Jellineck, D. et al., *Proc. Nat'l. Acad. Sci. USA* 90, 11227 (1993)); (6) adenosine triphosphate (Sassanfar, M. and Szostak, J. W., *Nature* 364, 550 (1993)); (7) theophylline (Jenison, R. D. et al., *Science* 263, 1425 (1994)); and (8) several amino acids (Farmulok, M. and Szostak, J. W., *J. Am. Chem. Soc.*, 114, 3990 (1992) and Connell, G. J. et al., *Biochemistry* 32, 5497 (1993)). Similarly, DNA and RNA nucleic acid ligands that bind to organic dyes have also been identified (Ellington, A. and Szostak, J., *Nature* 346, 618 (1990) and Ellington, A. and Szostak, *J., Nature* 355, 850 (1992)). Furthermore, nucleic acid ligands that bind other protein and small molecule targets will continue to be identified by use of the SELEX method taught in such publications as PCT International Publication No. WO 91/19813 and U.S. Pat. No. 5,270,163. Also, bi-directional nucleic acid ligand compounds which bind the target molecule, thrombin, have been identified and described in U.S. patent application Ser. No. 08/252,071, filed May 31, 1994. Another group of suitable receptor molecules are chemically modified derivatives of nucleic acid ligands, including derivatives having 2'-fluoro or 2'-amino substitutions on the ribose ring. These substitutions reduce degradation by ribonucleases. Additional possible chemical modifications include 2'-O-methyl derivatives, carbocyclic ribose analogs, thiophosphates, and modifications of the pyrimidine or purine bases. The nucleic acid ligands, chemically modified nucleic acid ligand derivatives, and bi-directional nucleic acid ligand compounds may be from 5 to 100 nucleotides in length, and are preferably between 15 and 40 nucleotides in length.

The spectroscopically detectable labels which may be attached to these new classes of receptor molecules for use in the present invention include fluorescent labels, energy transfer labels, luminescent labels, and near IR labels. Suitable fluorescent labels include fluorescein, fluorescein derivatives such as eosin, rhodamines such as Texas Red and tetramethylrhodamine, cyanine dyes such as thiazole orange, thiazole yellow and related dyes disclosed in U.S. Pat. Nos. 4,957,870 and 4,883,867, pyrene, porphyrin dyes such as LaJolla Blue and other dyes well known to practitioners in the art.

Suitable energy transfer labels include pairs of the above-described fluorescent labels with appropriately matched excitation and emission spectra for efficient energy transfer. An example is fluorescein and tetramethylrhodamine. Other appropriate examples and criteria for selection of appropriate dye pairs are known to those skilled in the art through references such as Morrison, L. E., Chapter 13 in *Nonisotopic DNA Probe Techniques* (Ed. Kricka, L. J., Academic Press (1992)). Suitable luminescent labels include dioxetanes, acridinium esters and luciferin.

Suitable near IR labels include LaJolla Blue dye, BODIPY dyes (commercially available from Molecular Probes, Inc. and dicyanine dyes.

Typically the spectroscopically detectable labels will be attached to the receptor molecule by chemical coupling of suitable reactive derivatives of the labels to suitable linkers or tethers such as commercially available amino-hexyl and amino propyl linking arms (available from Applied Biosystems, Clontech, Glen Research and other companies).

Reactive dye labels may also be attached to the receptor molecules by established linker methods to the C-5 of the pyrimidine or to the C-8 of purine rings. Such established linker methods are taught in references such as Goodchild, J., *Bioconjugate Chem.* 1, 165 (1990). One example of such direct internal labeling of a receptor molecule is a fluorescein labeled nucleic acid ligand prepared by iodoacetamido alkylation of the nucleic acid ligand. Briefly, using techniques taught in PCT Publication No. WO 94/02640, McLaughlin et al., *Nuc. Acids Res.* 20, 5205 (1992), and McLaughlin et al., *J. Am. Chem. Soc.* 114, 5509 (1992), a phosphorathioated nucleic acid ligand is constructed using standard solid phase oligonucleotide synthesis techniques with phosphoramidite reagents, and then reacted with 5-iodoacetamidofluorescein to yield a nucleic acid ligand labeled with fluorescein at a selected internal position.

Target molecules which are bound by spectroscopically detectable labeled receptor compounds of the present invention may include any compound of interest. Suitable target molecules can be a protein, peptide, cell surface marker, carbohydrate, polysaccharide, glycoprotein, hormone, receptor, antigen, antibody, co-factor, inhibitor, drug, dye, nutrient, growth factor, etc. without limitation.

Suitable samples which may be tested for target molecules include biological materials, foods, and environmental discharges such as liquid wastes, and biological materials including blood, plasma, serum, sputum, urine, semen, cerebro spinal fluid, bronchial aspirate, and macerated tissue.

Suitable spectroscopic detection methods which can be utilized with the spectroscopically detectable labeled receptor compounds of the present invention include fluorescence polarization, infrared (IR), near IR, luminescence, lifetime, and energy transfer techniques. The use of these techniques with spectroscopically detectable labeled receptor compounds offers a sensitive and simple method of measuring the binding of specific analytes or target molecules. The methods permit the use of nucleic acid ligands and other receptor molecules for both qualitative and quantitative binding measurements. Furthermore, use of the spectroscopically labeled nucleic acid ligands and other receptor molecules provides for direct signal generation without the need to separate bound from free labeled ligand. Specific advantages of utilizing spectroscopically labeled newer classes of receptor molecules as opposed to the more traditional antibodies include: (1) the lack of immunization of animals which is necessary for the production of antibodies; (2) the ability to relatively simply covalently attach spectroscopic dyes and other labels to the newer receptor molecules with higher specificity and at one or more locations all of which can not be accomplished easily with antibodies; (3) non-immunogenic or poorly immunogenic analytes or target molecules may be detected; (4) the synthesis or production of the newer receptor molecules, particularly nucleic acid ligands, is much simpler than the production of antibodies; and (5) as explained in greater detail above, the change in signal upon binding of a target molecule is larger in fluorescence polarization and anisotropy experiments due to the smaller size of the newer receptor molecules relative to the target molecules.

In fluorescence polarization and anisotropy, fluorescent molecules are excited by polarized light and their emission is also polarized. Detection of the polarization of the emission is accomplished by measuring the relative intensities of emission parallel to (Ipa) and perpendicular to (Ipe) the plane of polarized excitation light. Typically, the degree of depolarization of this emission is dependent upon solvent diffusion and tumbling of the fluorescent molecule and solution, thus changing its relationship to the plane of excitation light. In steady state measurements, polarization and anisotropy are defined by the following equations:

$$P(\text{polarization}) = \frac{Ipa - Ipe}{Ipa + Ipe}$$

$$r(\text{anisotropy}) = \frac{Ipa - Ipe}{Ipa + 2Ipe}$$

A change in polarization and anisotropy can be detected when the tumbling motion and/or environment of the fluorescently labeled newer receptor molecule changes. Such changes can occur upon binding to a target which increases the fluorescently labeled receptor molecules effective size and slows its tumbling.

Additional information about the fluorescently labeled receptor molecules behavior can be obtained by dynamic polarization techniques which determine the rate of anisotropy or polarization decay. These may be obtained through either time-resolved or phase-resolved techniques and may indicate more than one rotational process is contributing to the overall steady state behavior. Dynamic anisotropy and lifetime measurements are made by analyzing the decay of fluorescence intensity. These may be made either in the time domain (pulse method) or in the frequency domain (phase modulation method). Dynamic anisotropy measurements can be used to determine rotational correlation times. In general this value becomes larger as the rotational diffusion rate becomes slower. This increase can be correlated to binding of single stranded oligonucleotide dye conjugates to target molecules.

As stated above the spectroscopically detectable labeled receptor molecules of the present invention are useful for detecting the presence or absence of targets in biological samples, and for monitoring the binding of target compounds such as growth factors to their receptors in competition-based assays, and as such are useful in diagnostic assays. When used to detect the presence or absence of a target in blood, the spectroscopically detectably labeled receptor molecules may be introduced in solid or liquid form into blood collection devices such as the VACUTAINER™ brand blood collection tube. When the blood sample is then introduced into the blood collection device, the spectroscopically detectable labeled receptor molecules would disperse in the blood and bind to any target analytes that are present. This binding produces a spectroscopic change in intensity, polarization, or lifetime of a fluorescent label which would be diagnostic for the presence of the target.

This would represent a single-step diagnostic system where sample collection results in the generation of a diagnostic answer which is readable by an optics device. Examples of suitable readouts include fluorescence polarization anisotropy and fluorescence lifetime spectroscopy to extract a signal indicating the amount of target present in blood, serum or plasma. Furthermore, this single-step diagnostic system need not be restricted to fluorescence. In addition, a chemical change which occurs upon binding may trigger a change in fluorescent properties. Therefore, the use of infrared (IR) fluorescent dyes in wave-length ranges which do not absorb or fluoresce in the specimens may also be very useful.

Previous attempts to perform homogeneous assays using antibody reagents have had limited success due to difficulties in controlling the site of attachment for the fluorescent label. It is well known in the art that the fluorescent label should be located close to the antibody binding site. Since antibodies are derived from biological sources, it is difficult to control the site where the fluorescent label is introduced. Consequently, the performance of these reagents has been poor. In contrast, nucleic acid ligands and other of the newer receptor molecules are synthetically derived. Therefore, the fluorescent label may be introduced into any site during the synthesis of these reagents. This ability to control the site of attachment promises significant enhancements in the performance of homogeneous fluorescent detection methods.

Furthermore, spectroscopically detectable labeled nucleic acid ligands may also be prepared by techniques known as blended SELEX which are taught in U.S. patent application Ser. No. 08/234,997, filed Apr. 28, 1994 the disclosure of which is specifically incorporated herein by reference.

In one preferred embodiment of the blended SELEX process, the spectroscopically detectable nucleic acid ligand is prepared by performing the SELEX method utilizing an initial candidate mixture wherein each nucleic acid sequence of the candidate mixture has attached thereto a spectroscopically detectable label. This mixture is referred to as a "blended candidate mixture". This may be accomplished using a candidate mixture wherein each nucleic acid sequence of the candidate mixture has 1) a single spectroscopically detectable label attached at either the 5' or 3' end of nucleic acid sequence, 2) spectroscopically detectable labels at both the 5' and 3' ends of the nucleic acid sequence, 3) spectroscopically detectable labels added to individual nucleic acid residues, 4) spectroscopically detectable labels attached to all or a portion of all pyrimidine or purine residues, or 5) spectroscopically detectable labels attached to all or a portion of all nucleotides of a given type. The spectroscopically detectable labels may also be attached only to the fixed or to the randomized regions of each nucleic acid sequence of the candidate mixture.

The invention is further described by the following examples which are offered by way of illustration and are not intended to limit the invention in any manner. In these examples all percentages are by weight if for solids and by volume if for liquids or are used to refer to reaction yields, and all temperatures are in degrees Celsius unless otherwise noted.

EXAMPLE 1

Preparation of Spectroscopically Detectable Labeled

Nucleic Acid Ligands that Bind Thrombin

Both fluorescein-labeled nucleic acid ligands and thiazole orange-labeled nucleic acid ligands were prepared as examples of spectroscopically detectable labeled nucleic acid ligands.

The fluorescein-labeled nucleic acid ligands that bind thrombin were synthesized with an ABI 380B synthesizer (Applied Biosystems, Inc., Foster City, Calif.) using standard reagents supplied by the manufacturer and ABI 6-FAM amidite (C6 linked fluorescein). The fluorescein-labeled nucleic acid ligands were then purified by standard polyacrylamide gel electrophoresis techniques unless otherwise noted.

Preparation of Thiazole Orange ("TO") N-hydroxysuccinimide ester

3-( 1-(4-methyl-quinolinium))-propionic acid (1)

Lepidine (2.95 gm, Aldrich) was mixed with 4.13 gm iodopropionic acid (Aldrich) neat. This mixture was heated at 80° C. for three hours under argon in an oil bath. The solid that formed was triturated with dicholoromethane and collected by filtration to give 1 as 5.2 gm of yellow solid (73%): $^1H$ NMR (DMSO-$d_6$): ppm 3.01 (s,3H), 3.08 (t, 2H), 5.21 (t, 2H), 8.07 (m, 2H), 8.28 (t, 1H), 8.57 (dd, 2H), 9.43 (d, 1H), 12.5 (br s, 1H); $^{13}C$ NMR (DMSO-d6) ppm 19.8, 33.3, 52.8, 119.2, 122.4, 127.2, 128.9, 129.5, 135.2, 136.7, 149.3, 159.0, 171.4; LRMS ($FAB^+$, glycerol) M+=216 m/z.

(4-[3-methyl-2,3-dihydro-(benzo-1,3-thiazole)-2-methylidene]-1-quinolinium)-3-propionic acid (2)

1-(4-Methyl-quinoline)-propionic acid (1.0 g) and 1.0 g N-methyl-benzothiazole-thiomethyl tosylate (Bader) were mixed together in 15 ml ethanol in a 50 mL round bottom flask. Triethylamine (0.1 mL) was added. Almost immediately the reaction mixture turned bright red. The reaction mixture was heated at reflux for two hours and cooled to room temperature. A red solid was isolated from the resulting (and foul smelling) solution. The yield of this material was 900 mg (47%) and only showed one spot near the origin on thin layer chromatography (silica gel, 9:1 dichloromethane/methanol). NMR ($CD_3OD$) $^1H$ ppm: 1.31 (t, 2H), 2.86 (t, 2H), 3.20 (t, 2H), 3.31 (s, 2H), 3.90 (s, 3H), 4.76 (t, 1H), 6.74 (s, 1H), 7.30, (m, 2H), 7.73, (m, 7H), 8.47 (dd, 2H); $^{13}C$ NMR ($CD_3OD$) ppm: 8.9, 20.0, 33.7, 38.0, 51.0, 88.8, 109.2, 113.3, 118.6, 125.5, 126.3, 126.7, 127.7, 129.0, 129.4, 134.1, 141.6, 145.4, 180.7, 189.8, 194.0; LRMS (FAB+, glycerol) M+=363 m/z ($C_{21}H_{19}N_2O_2S$).

(4-[3 -methyl-2,3 -dihydro-(benzo-1, 3-thiazole)-2-methylidene]-1-quinolinium)-3-propionic acid N-hydroxysuccinimide ester (3)

2 (100 mg) and 125 mg 1,3-dicyclohexylcarbodiimide (DCC, Fluka) were added to a dry mixture of dichlormethane, tetrahydrofuran, and N, N dimethyl foramide and allowed to stir one hour at room temperature under argon. After one hour, 65 mg of N-hydroxy-succinimide was added and stirring continued overnight. The dark red solution was filtered leaving the desired NHS ester in solution. Solvents were removed under high vacuum conditions to yield a glossy solid. This solid was dissolved in dichloromethane and 2-propanol and stored in a refrigerator. Two fractions were isolated for a total recovery of 50 mg (~40%). Both fractions were analyzed by Low Resolution Mass Spectrometry (LRMS), Fast Atom Bombardment ($FAB^+$) in glycerol. Both fractions showed $M^+$ of 460, though the first fraction was more pure. The second fraction contained a higher molecular weight impurity suggested by a peak at 569 m/z. High resolution FAB+ MS confirmed the identity of the molecular ion for the first fraction: 460.13296 m/z; calculated for $C_{25}H_{22}N_3O_4S$: 460.13276.

Preparation of TO-oligonucleotide conjugate

A thiazole orange-labeled nucleic acid ligand was then prepared by first preparing the unlabeled nucleic acid ligand (SEQ ID NO: 1) coupled to an aminopropyl (C3) linker arm with an ABI 380B synthesizer and protected phosphoramidite reagents from Glen Research (Sterling, Va.). Purification and deprotection of the nucleic acid ligand with C3 linker arm was accomplished by treatment with concentrated ammonium hydroxide at 55° C. for six hours. Following filtering, the product mixture and evaporation of the solvent at high vacuum, the nucleic acid ligand with C3 linker arm was ethanol precipitated. The reactive primary amino on the linker arm of the nucleic acid ligand was then reacted with the thiazole orange N-propionic acid NHS ester (3). Specifically, a 10 μl aliquot of thiazole orange NHS ester ("TONHS") solution (5.9 mg TO/150 μg DMSO (d6) (85.5 mM)) was added to a diluted (0.125 μM) nucleic acid ligand solution (50 μl of nucleic acid ligand (0.25 μM) in $H_2O$ diluted with 50 μl buffer $Na_2CO_3/NaH_2O$ 250 mM). The mixture was vortexed in an Eppendorf tube, covered with aluminum foil and allowed to sit at room temperature for 15 hours. The crude dye labeled nucleic acid ligand was then purified by passing through a PD-10 column (Pharmacia) to remove unreacted dye, followed by purification by an OPC cartridge (ABI) to remove unlabeled nucleic acid ligand. The OPC cartridge purification technique is well known to those skilled in the art from references such as McBride, L. J. et al. *BioTechniques* 6, 362 (1988). The thiazole orange-labeled SEQ ID NO: 1 was referred to as Compound 3 (see FIG. 1). The sequences of the specific thrombin-binding nucleic acid ligands which were labeled were:

(1) 5'-GGTTGGTGTGGTTGG-3' (SEQ ID NO: 1); and (2) 5'-CAGTCCGTGGTAGGGCAGGTTGGGGTGA-CTTCGTGGAA-3' (SEQ NO: 2).

The fluorescein-labeled SEQ ID NO: 1 was referred to as Compound 1 and the fluorescein-labeled SEQ ID NO: 2 was referred to as Compound 2 (see FIG. 1).

Similarly, a control spectroscopically detectable labeled nucleic acid ligand (Compound 4) was prepared using the same techniques. The sequence of this control was a scrambled version of SEQ ID NO: 1, particularly: 5'-GGTGGTGGTTGTGGT-3' (SEQ ID NO: 3), and was labeled with fluorescein through the C6 linker arm.

EXAMPLE 2

Preparation of Spectroscopically Detectable Labeled

Nucleic Acid Ligand that Binds Elastase

A fluorescein-labeled nucleic acid ligand that binds elastase was synthesized using the same techniques as were used in Example 1. The fluorescein was attached to the following nucleic acid ligand sequence through the C6 linker arm.

Sequence of elastase-binding nucleic acid ligand:

5'-TAGCGATACTGCGTGGGTTGGGGCGGGTAGGG-CCAGCAGTCTCGT-3' (SEQ ID NO: 4)

The fluorescein-labeled SEQ ID NO: 4 was referred to as Compound 5 (see FIG. 1).

The same techniques used in Example 1 can also be used to spectroscopically detectably label other nucleic acid ligands such as nucleic acid ligands that bind the cell surface marker CD4, basic fibroblast growth factor, vascular endothilial growth factor and human chorionic gonadotropin.

EXAMPLE 3

Fluorescence Polarization Assays Using Spectroscopically

Detectable Labeled Nucleic Acid Ligands

The Compounds prepared in Examples 1 and 2 were tested in fluorescence polarization assays as set forth below.

Compound 1

A thrombin solution was prepared from human alpha-thrombin (American Diagnostics) at 100 nM for the highest concentration of thrombin in a buffer of 140 mM NaCl, 20 mM tris acetate, 1 mM $CaCl_2$, 5 mM KCl, 1 mM $MgCl_2$, pH 7.4. Serial dilutions of this solution were then prepared to give a range of concentrations from 0.015 nM to 100 nM. Similarly, a solution of human serum albumin ("HSA") (Sigma) was prepared at 247 nM as the highest concentration with the same buffer and then serially diluted to give a concentration range down to 0.39 nM.

Figure 2:
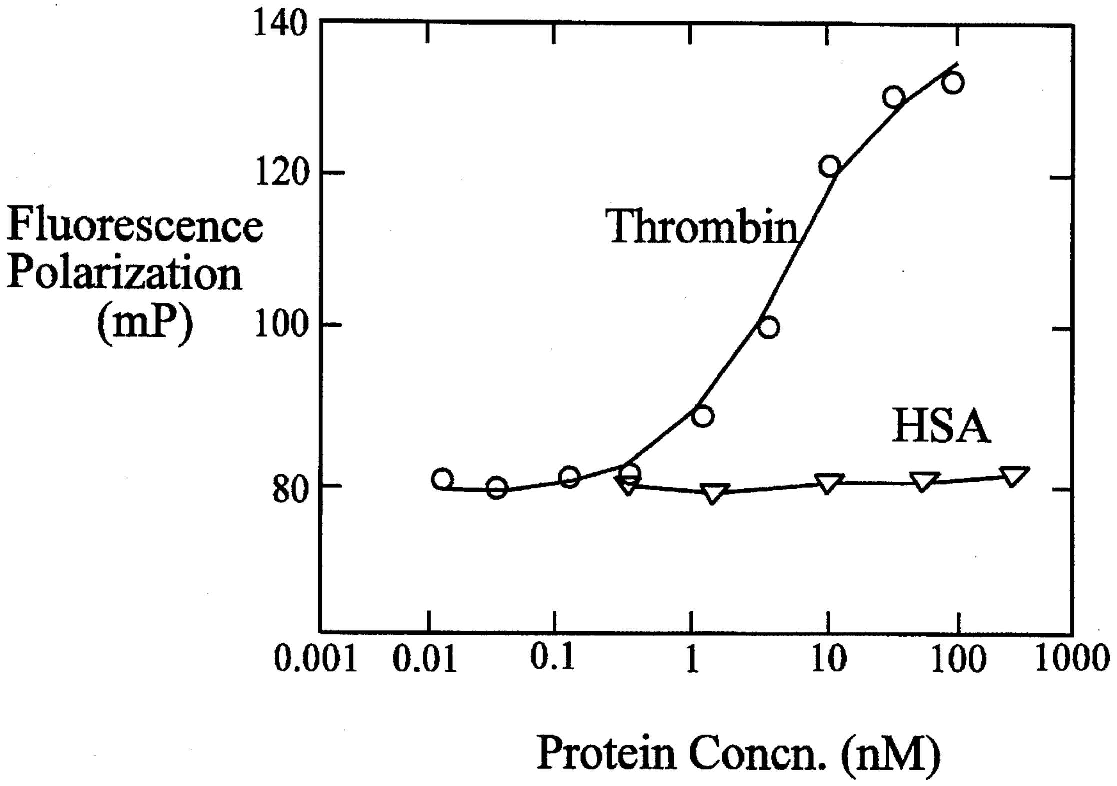
FIG. 2 is a graph of the results of an assay for thrombin using a fluorescein-labeled nucleic acid ligand with human serum albumin as a control.

Compound 1 was added to a sample of each dilution of thrombin solution and HSA solution to a concentration of 6.4 nM, then vortexed and let stand at room temperature for 15 minutes before fluorescence measurement as described below. The results of the fluorescence assay are presented in FIG. 2 and show detectable binding of Compound 1 to thrombin, but not to HSA.

Compound 2

A thrombin solution was prepared at 100nM for the highest concentration in the same buffer as was used for Compound 1. Serial dilutions of this solution were then prepared to give a range of concentrations from 0.0051 nM to 100 nM. Similarly, a HSA solution was prepared at 150 nM as the highest concentration and serially diluted in the same buffer as the thrombin solution down to 1.2 nM.

Figure 3:
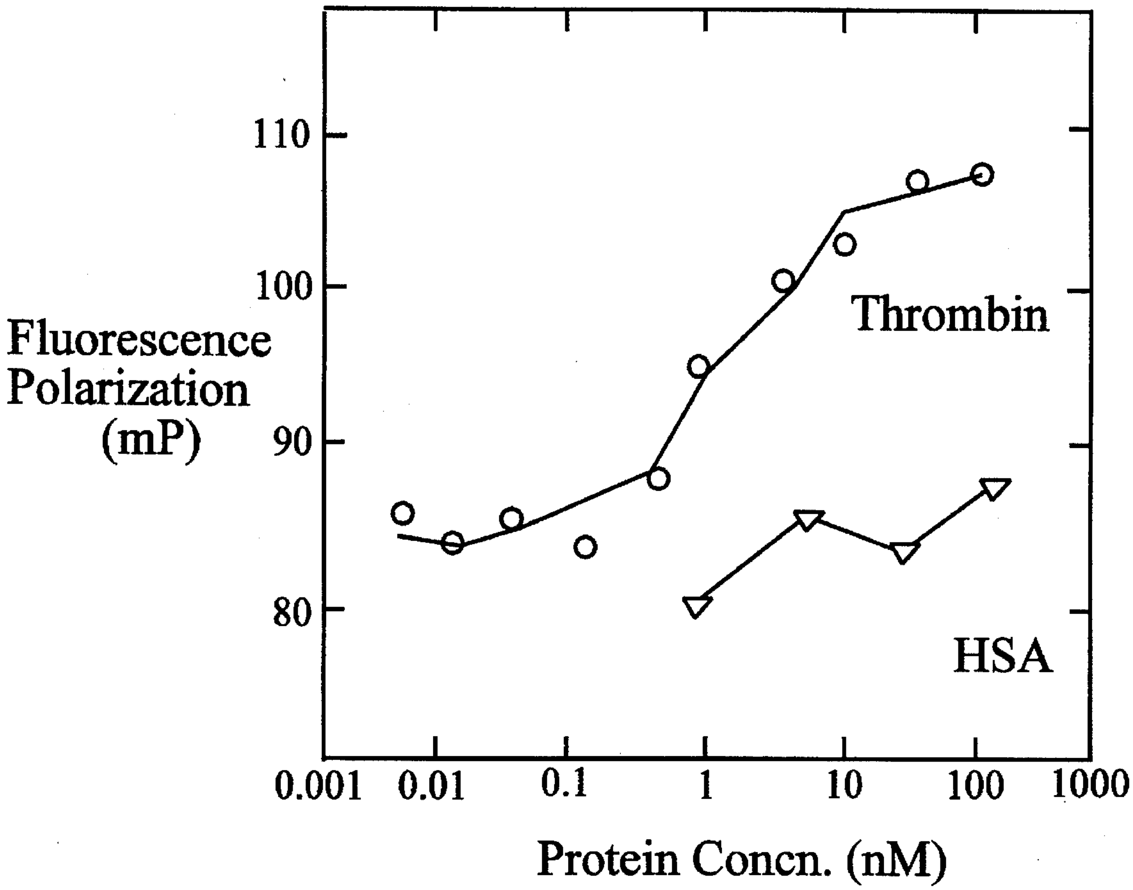
FIG. 3 is a graph of the results of an assay for thrombin using a fluorescein-labeled nucleic acid ligand with human serum albumin as a control.

Compound 2 was then added to a sample of each dilution of thrombin solution and HSA solution to a concentration of 0.62 nM, then vortexed and let stand at room temperature for 15 minutes before fluorescence measurement as described below. The results of the fluorescence assay are presented in FIG. 3 and show detectable binding of Compound 2 to thrombin, but not to HSA.

Compound 3

A thrombin solution was prepared at 660 nM for the highest concentration in the same buffer as was used for Compound 1. Serial dilutions of this solution were prepared to give a range of concentrations from 0.14 nM to 660 nM. Similarly, a HSA solution was prepared at 660 nM as the highest concentration and serially diluted in the same buffer as the thrombin solution down to 11.1 nM.

Figure 4:
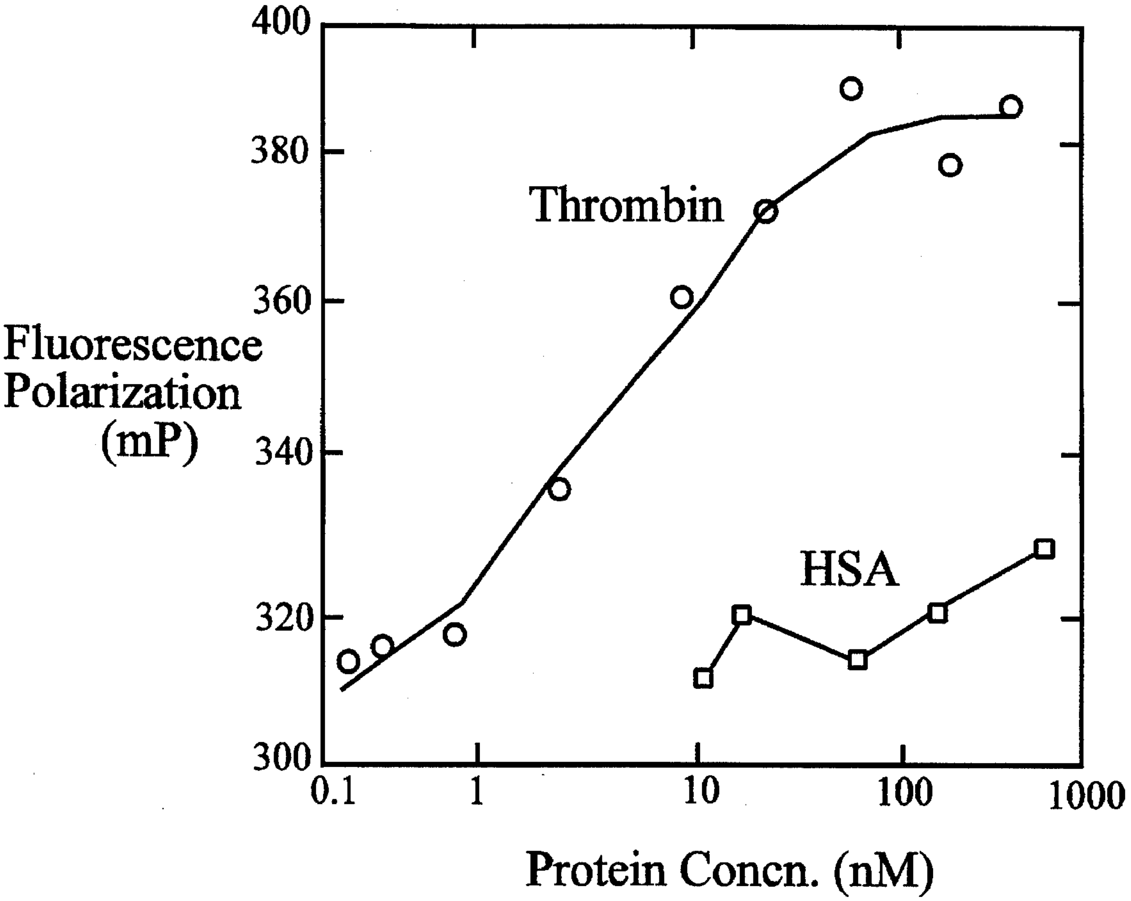
FIG. 4 is a graph of the results of an assay for thrombin using a thiazole orange-labeled nucleic acid ligand with human serum albumin as a control.

Compound 3 was then added to a sample of each dilution of thrombin solution asd HSA solution to a concentration of 8 nM, then vortexed and let stand at room temperature for 15 minutes before fluorescence measurement as described below. The results of the fluorescence assay are presented in FIG. 4 and show detectable binding of Compound 3 to thrombin, but not to HSA.

Compound 4

Compound 4 was the control prepared in Example 1, and as such was added to the thrombin dilutions and HSA dilutions at the same respective concentrations of Compounds 1, 2 and 3 above. Similarly, Compound 4 was then subjected to the same conditions as Compounds 1, 2 and 3, and analyzed with an SLM instrument to determine anisotropy values as described in Example 4 below. Compound 4 did not show detectable binding to thrombin or HSA in the fluorescence anisotropy assay.

Compound 5

An elastase solution was prepared from human neutrophil elastase (Athens Research Technology) at 180 nM for the highest concentration in a buffer of 150 mM NaCl, 2 mM $MgCl_2$, 6 mM KCl, 10 mM TRIS, pH 7.0. Serial dilutions of this solution were then prepared to give a range of concentrations from 0.027 nM to 180 nM.

Figure 5:
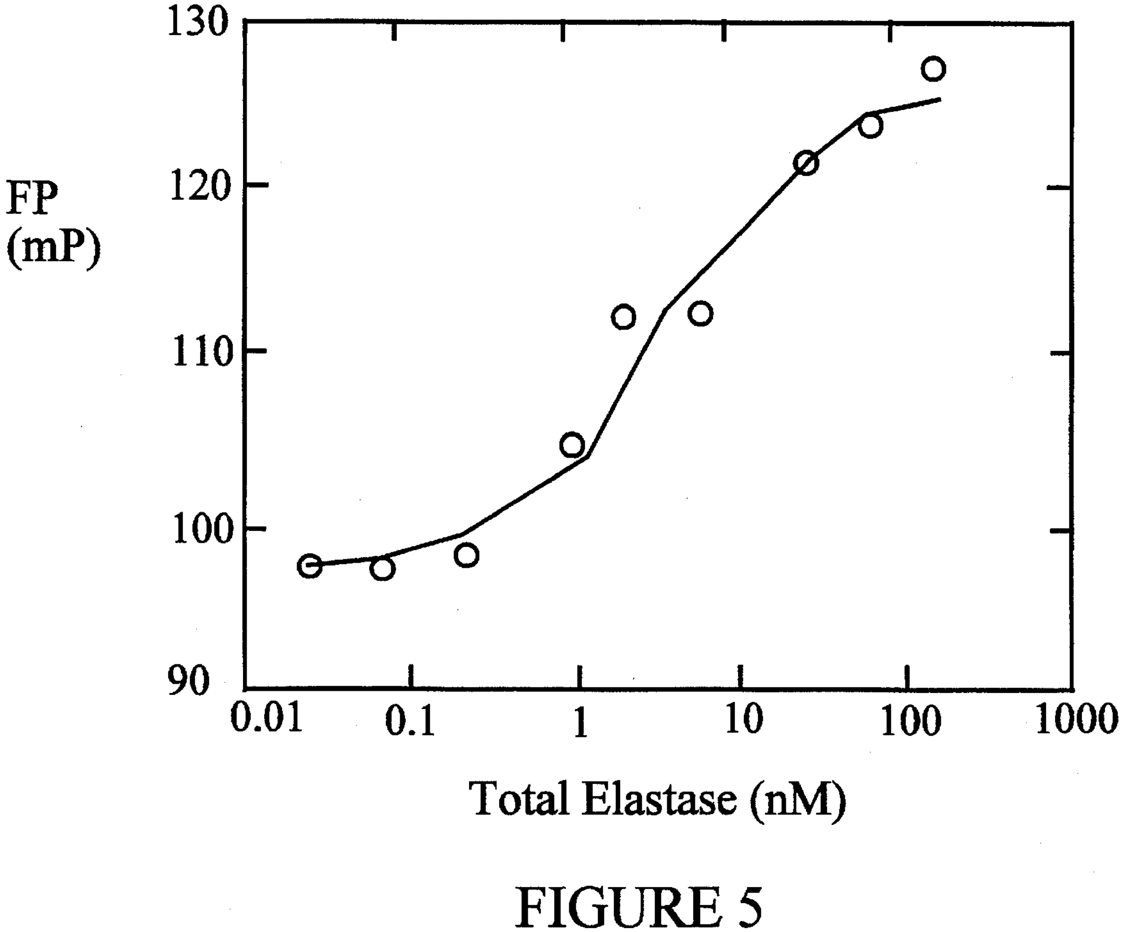
FIG. 5 is a graph of the results of an assay for elastase using a fluorescein labeled nucleic acid ligand.

Compound 5 was then added to a sample of each dilution of elastase solution to a concentration of 1.5 nM, then vortexed and let stand at room temperature for 15 minutes before fluorescence measurement as described below. The results of the fluorescence assay are presented in FIG. 5 and show detectable binding of Compound 5 to thrombin.

Fluorescence Measurement

The preparations of Compounds 1, 2, and 3 in thrombin dilutions and HSA dilutions and the preparations of Compound 5 in elastase dilutions were then analyzed with a Jolley FPM-1 fluorometer. The fluorometer uses an L-format and was equipped with standard interference filters appropriate for fluoresceins' emission and excitation maxima. The same filters were used with the Compound 3 preparations even though it had a thiazole orange label.

The fluorescence polarization of the reaction mixtures was measured directly using 12×75 mm borosilicate glass test tubes. The maximum change in fluorescence polarization was reported as ΔmP (millipolarization units). As reported below in Table 1, the data represent the average of three readings at ambient temperature.

TABLE 1

FLUORESCENCE POLARIZATION DETECTION NUCLEIC ACID LIGAND ASSAYS

| Compound | Dye/Linker | Target | Δ mP | Kd (nM) |
|---|---|---|---|---|
| 1 | 5'-fluorescein C6 linker | Thrombin | +52 | 2.0 |
| 3 | 5'-Thiazole Orange C3 linker | Thrombin | +80 | 5.7 |
| 2 | 5'-fluorescein C6 linker | Thrombin | +25 | 1.5 |
| 5 | 5'-fluorescein C6 linker | Elastase | +30 | 2.6 |

The values reported in Table 1 evidence significant changes in fluorescence polarization (ΔmP) which correlates to binding of the spectroscopically detectably labeled nucleic acid ligands to target (Kd). Similar changes in fluorescence polarization can be expected from similarly labeled nucleic acid ligands based on the difference in size of the ligand/target complex as compared to the ligand alone.

EXAMPLE 4

Anisotropy Assays Using Spectroscopically

Detectable Labeled Nucleic Acid Ligands

The preparations from Example 3 were also analyzed using an SLM instrument to determine anisotropy values.

These values are reported in Table 2 below.

TABLE 2

| Steady State Anisotropy | |
|---|---|
| Sample | r (anisotropy) |
| Compound 4 (Control) | 0.0403 ± 0.0003 |
| Compound 4 + thrombin solution | 0.0445 ± 0.0006 |
| Compound 1 | 0.04429 ± 0.0096 |
| Compound 1 + HSA solution (negative control) | 0.04433 ± 0.0074 |
| Compound 1 + thrombin solution | 0.08687 ± 0.0017 |

| Rotational correlation time φ from dynamic anisotropy: | |
|---|---|
| Sample | φ (ns)* |
| Compound 4 (control) | 0.214 |
| Compound 4 + thrombin solution | 0.240 |
| Compound 1 | 0.202 |
| Compound 1 + HSA solution (negative control) | 0.195 |
| Compound 1 + thrombin | 0.497 |

*Single component fit to the dynamic anisotropy spectra with SLM software.

The values reported in Table 2 show a detectable difference in anisotropy between free nucleic acid ligand (Compound 1 above) and the complex of nucleic acid ligand bound to target (Compound 1+thrombin solution). As with the fluorescence polarization values in Table 1 (Example 3), similar differences in anisotropy values can be expected for other spectroscopically detectably labeled nucleic acid ligands when bound to their targets as compared to unbound anisotropy values.

EXAMPLE 5

Preparation of Phosphorothioate-Fluorescein Labeled

Nucleic Acid Ligand that Binds Thrombin

Standard solid phase oligonucleotide techniques with phosphoramidite reagents were used to prepare a sequence having SEQ ID NO: 1 with a phosphorothioate group incorporated between G6 and T7 (i.e. 5'-GGTTGG$_x$TGTGGTTGG-3', where x indicates the position of the phosphorothioate). The techniques for preparation of phosphorothioates are well known to those in the art from references such as Eckstein, F., *Annul. Rev. Biochem.* 54, 367 (1985).

The crude phosphorothioate oligomer was then ethanol precipitated and redissolved in 50 mM potassium phosphate (pH 7.0). A solution of 5-iodoacetamidofluorescein (100 uL, 10 mg/mL in DMF) was added to a solution of the phosphorothioate oligomer (300 ug in 200 uL of 50 mM potassium phosphate buffer) and mixed gently. The resulting solution was allowed to stand at room temperature for 24 hours at which time a freshly prepared solution of 5-iodoacetamidofluorescein (100 uL, 10 mg/mL in DMF) was again added. After three hours, the resulting solution was stored at −20° C. for three days until purified.

Additional 50 mM potassium phosphate buffer (700 uL) was added and the mixture separated over a NAP-25 size exclusion column (Pharmacia) previously equilibrated with TRIS-EDTA buffer. The fluorescent fraction which eluted in the void volume (1.4 mL total) was collected and concentrated to 100 uL in vacuo. Sequencing gel sample buffer was added, and the sample separated on an 8% sequencing gel. This phase of the purification was not very effective since the oligomer migrated with the salt front in the gel. The fluorescent band was excised, eluted from the gel, and ethanol precipitated. The resulting pellet was taken up in 1 mL of 0.1M TEAA buffer and purified over an OPC column (Applied Biosystems) according to the manufacturer's protocol.

These same techniques can be used to internally spectroscopically detectably label other nucleic acid ligands such as nucleic acid ligands that bind the cell surface marker CD4, basic fibroblast growth factor, vascular endothelial growth factor and human chorionic gonadotropin.

A thrombin solution was prepared at 600 nM for the highest concentration in the same buffer as was used for Compound 1 in Example 3. Serial dilutions of this solution were then prepared to give a range of concentrations from 0.045 nM to 600 nM. Similarly, a HSA solution was prepared at 1080 nM as the highest concentration and serially diluted in the same buffer as the thrombin solution down to 1.5 nM.

Figure 6:
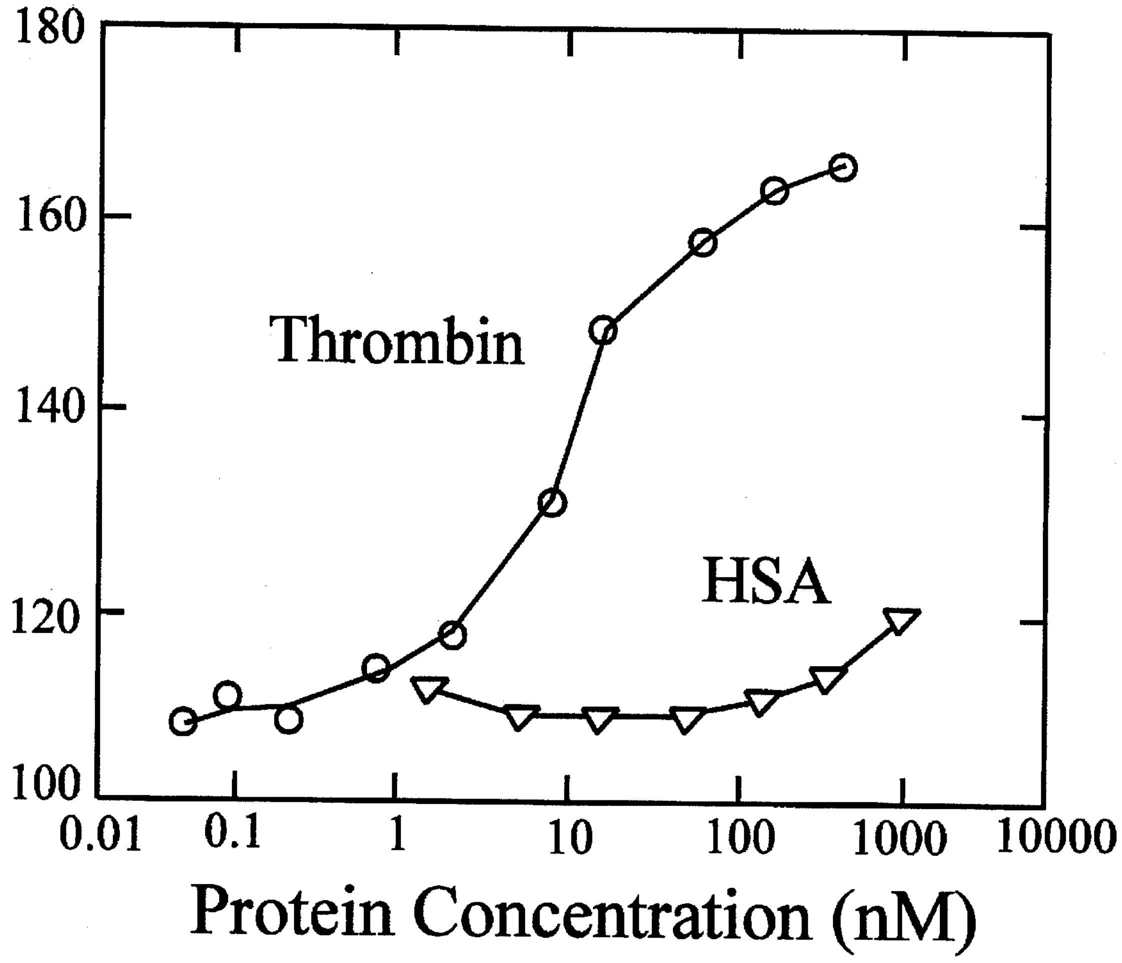
FIG. 6 is a graph of the results of an assay for thrombin using a nucleic acid ligand internally labeled with fluorescein with human serum albumin as a control.

Compound 6 was then added to a sample of each dilution of thrombin solution and HSA solution to a concentration of 2.3 nM, then vortexed and let stand at room temperature for 15 minutes before fluorescence measurement was taken as described in Example 3. The data from the measurements is presented below as the average of three readings at ambient temperature. The results of the assay are also presented in FIG. 6 which shows detectable binding of Compound 6 to thrombin, but not to HSA.

| Compound | Dye/Linker | Target | Δ mP | Kd (nM) |
|---|---|---|---|---|
| 6 | Fluorescein tethered at T7 phosphorothioate via iodoacetamide | Thrombin | +55 | 11.1 |

Similar changes in fluorescence polarization can be expected from similarly internally labeled nucleic acid ligands based on the difference in size of the ligand/target complex as compared to the ligand alone.

The invention disclosed herein is not limited in scope to the embodiments disclosed herein. Appropriate modifications, adaptations and expedience for applying teachings herein in individual cases can be employed and understood by those skilled in the art, within the scope of the invention as claimed herebelow.

What is claimed is:

1. A method for determining the presence of a target compound in a sample, said target compound selected from the group consisting of proteins, peptides, cell surface markers, carbohydrates, polysaccharides, glycoproteins, hormones, receptors, antigens, antibodies, co-factors, inhibitors, drugs, dyes, nutrients, growth factors, amino acids, ATP, theophylline, whole cells and viral particles comprising:

(a) measuring at least one of the fluorescence polarization, anisotropy values or rotational correlation times of a spectroscopically detectable labeled nucleic acid ligand to said target compound, (b) adding to the sample the spectroscopically detectable labeled nucleic acid ligand whereby the nucleic acid ligand binds to the target compound; and (c) determining whether there is a difference between at least one of the fluorescence polarization, anisotropy values or rotational correlation times of (i) the mixture of spectroscopically detectable nucleic acid ligand bound to the target compound and sample in (b), and (ii) the spectroscopically detectable nucleic acid ligand alone in (a) whereby an increase in at least one of the fluorescence polarization, anisotropy values or rotational correlation times in the mixture relative to the nucleic acid ligand alone is indicative of the presence of the target compound in the sample.

2. The method of claim 1 wherein the spectroscopically detectable nucleic acid ligand is labeled with fluorescein.

3. The method of claim 2 wherein the fluorescein label is attached to the nucleic acid ligand at its 3' end.

4. The method of claim 2 wherein the fluorescein label is attached to the nucleic acid ligand at its 5' end.

5. The method of claim 4 wherein the nucleic acid ligand binds thrombin.

6. The method of claim 5 wherein the spectroscopically detectable labeled nucleic acid ligand has the formula of Compound 1.

7. The method of claim 5 wherein the spectroscopically detectable labeled nucleic acid ligand has the formula of Compound 2.

8. The method of claim 2 wherein the fluorescein label is attached at an internal position on the nucleic acid ligand.

9. The method of claim 8 wherein the nucleic acid ligand binds thrombin.

10. The method of claim 9 wherein the spectroscopically detectable nucleic acid ligand has the formula of Compound 6.

11. The method of claim 1 wherein the nucleic acid ligand is labeled with thiazole orange.

12. The method of claim 11 wherein the thiazole orange label is attached to the nucleic acid ligand at its 3' end.

13. The method of claim 11 wherein the thiazole orange label is attached at an internal position on the nucleic acid ligand.

14. The method of claim 11 wherein the thiazole orange label is attached to the nucleic acid ligand at its 5' end.

15. The method of claim 5 wherein the spectroscopically detectable labeled nucleic acid ligand has the formula of Compound 3.

16. The method of claim 4 wherein the nucleic acid ligand binds elastase.

17. The method of claim 16 wherein the spectroscopically detectable labeled nucleic acid ligand has the formula of Compound 5.

18. The method of claim 1 wherein the spectroscopically detectable labeled nucleic acid ligand is a bi-directional nucleic acid ligand.

19. The method of claim 1 wherein the determination of step (c) is made by comparison of fluorescence polarization values of (i) and (ii).

20. The method of claim 1 wherein the determination of step (c) is made by comparison of anisotropy values of (i) and (ii).

21. The method of claim 1 wherein the determination of step (c) is made by comparison of rotational correlation times of (i) and (ii).

22. The method of claim 1 wherein the sample is a biological sample.

23. The method of claim 22 wherein the sample is blood.

24. The method of claim 1 wherein the target compound is thrombin.

25. The method of claim 1 wherein the target compound is elastase.

26. The method of claim 1 wherein the target compound is a cell surface marker.

27. The method of claim 1 wherein the target compound is a growth factor.

28. The method of claim 27 wherein the target compound is basic fibroblast growth factor.

29. The method of claim 27 wherein the target compound is vascular endothelial growth factor.

30. The method of claim 1 wherein the target compound is a growth factor receptor.

31. The method of claim 1 wherein the target compound is human chorionic gonadotropin.

32. The method of claim 1 wherein the target compound is a whole cell.

33. The method of claim 32 wherein the whole cell is a bacterial cell.

34. The method of claim 1 wherein the target compound is a viral particle.

35. A method of monitoring the binding of a target compound to its receptor in a sample using a spectroscopically detectable nucleic acid ligand to the receptor in a competition-based assay, comprising:

(a) measuring the spectroscopic emissions of the spectroscopically detectable nucleic acid ligand;

(b) mixing the spectroscopically detectable nucleic acid ligand with the sample, whereby the spectroscopically detectable nucleic acid ligand binds to the receptor in competition with the target compound;

(c) measuring the spectroscopic emissions of the complex of the spectroscopically detectable nucleic acid ligand bound to the receptor of step (b);

(d) determining the degree of binding of the spectroscopically detectable nucleic acid ligand to the receptor from the spectroscopic emissions measured in step (c); and (e) calculating the degree of binding of target compound to its receptor from the determination of step (d).

36. The method of claim 35 wherein the target compound is a growth factor. b1 In this embodiment, the method comprises the steps of adding to the sample a spectroscopically detectable labeled nucleic acid ligand that binds to the receptor; measuring the spectroscopic emissions of the complex of receptor and spectroscopically detectable nucleic acid ligand; determining from the spectroscopic emissions of the complex the degree of binding of the spectroscopically detectable labeled nucleic acid ligand to the receptor; and calculating from the degree of binding of the spectroscopically detectable labeled nucleic acid ligand to the receptor, the degree of binding of target compound to the receptor.

* * * * *